(12) United States Patent
Melman

(10) Patent No.: US 8,722,102 B2
(45) Date of Patent: May 13, 2014

(54) COMPOSITIONS FOR TREATMENT OF SKIN AND EAR INFECTIONS

(75) Inventor: Steven A. Melman, Boca Raton, FL (US)

(73) Assignee: Dechra Veterinary Products LLC, Overland Park, KS (US)

(*) Notice: Subject to any disclaimer, the term of this patent is extended or adjusted under 35 U.S.C. 154(b) by 0 days.

(21) Appl. No.: 13/018,388

(22) Filed: Jan. 31, 2011

(65) Prior Publication Data

US 2012/0027875 A1 Feb. 2, 2012

Related U.S. Application Data

(60) Provisional application No. 61/299,889, filed on Jan. 29, 2010.

(51) Int. Cl.
| | | |
|---|---|---|
| *A61K 33/22* | (2006.01) | |
| *A61K 31/4164* | (2006.01) | |
| *A61P 31/00* | (2006.01) | |
| *A61P 29/00* | (2006.01) | |
| *A61P 17/04* | (2006.01) | |
| *A61P 31/10* | (2006.01) | |
| *A61K 31/573* | (2006.01) | |
| *A61P 31/04* | (2006.01) | |

(52) U.S. Cl.
USPC .................... 424/659; 514/171; 514/399

(58) Field of Classification Search
None
See application file for complete search history.

(56) References Cited

U.S. PATENT DOCUMENTS

| | | | | |
|---|---|---|---|---|
| 5,110,809 | A | * | 5/1992 | Wang et al. ................ 514/171 |
| 5,461,068 | A | * | 10/1995 | Thaler et al. .............. 514/399 |
| 5,480,658 | A | | 1/1996 | Melman |
| 5,536,742 | A | | 7/1996 | Mason |
| 5,643,937 | A | | 7/1997 | Mason |
| 5,853,767 | A | | 12/1998 | Melman |
| 2004/0033208 | A1 | * | 2/2004 | Cagle et al. ............. 424/78.02 |
| 2004/0120954 | A1 | * | 6/2004 | Seiki et al. ................ 424/146.1 |
| 2006/0046970 | A1 | * | 3/2006 | Bowman et al. ............. 514/28 |
| 2007/0078116 | A1 | * | 4/2007 | Lane ........................... 514/171 |
| 2008/0317737 | A1 | | 12/2008 | Patel et al. |

OTHER PUBLICATIONS

Malacetic Ultra Flush for Dogs, Cats, and Horses (2 oz.), Nov, 6, 2009. http://www.entirelypets.com/malaceticultraflush20z.html.*

* cited by examiner

*Primary Examiner* — Scott Long
*Assistant Examiner* — Sarah Alawadi
(74) *Attorney, Agent, or Firm* — Berenato & White, LLC

(57) ABSTRACT

The present invention relates to a composition for the treatment of skin and ear infections in humans and animals such as dogs, cats and horses. In particular, the present invention relates to a topical composition comprising acetic acid, an antibacterial and/or an anti-fungal, and preferably also an anti-inflammatory. More specifically, the composition of the present invention is a bandage, bedding, clothing, conditioner, cream, drape, dressing, film, foam, gauze, gel, lotion, mousse, otic solution, pad, patch, serum, shampoo, solution, spray, or wipe for treatment or prevention of skin infections, wherein the composition comprises about 0.1-10% acetic acid, about 0.1-10% boric acid, about 0.01-20% azole, and optionally about 0.01-20% corticosteroid.

3 Claims, No Drawings

COMPOSITIONS FOR TREATMENT OF SKIN AND EAR INFECTIONS

CROSS-REFERENCE TO RELATED APPLICATIONS

This application claims priority to U.S. Provisional Application No. 61/299,889 filed Jan. 29, 2010.

FIELD OF INVENTION

The present invention relates to a composition for the treatment of skin and ear infections in humans and animals such as dogs, cats and horses. In particular, the present invention relates to a topical composition comprising acetic acid, an antibacterial and/or an anti-fungal, and preferably also an anti-inflammatory. More specifically, the present invention relates to a composition that combines the antimicrobial effects of acetic and boric acid with the antifungal effects of an azole, preferably with the antipruritic effects of a topical steroid. The present invention also relates to a method of treating a skin or ear infection in a human or an animal comprising administering an effective amount of a composition comprising acetic acid, an antibacterial and/or an anti-fungal, and preferably also an anti-inflammatory to the affected area.

BACKGROUND OF INVENTION

There are many products on the market today to treat skin and ear infections.

U.S. Pat. No. 5,480,658, which is incorporated herein by reference, discloses a preferably pH balanced multi-purpose cleaning solution containing acetic acid and boric acid in a water base, useful on pets for the routine cleaning of the ear, the cleaning of the sensitive ear, particularly for cleaning moist, waxy or odiferous ears, the prevention and treatment of ear disease such as Swimmer's Ear and other ear diseases, acidification of the ear, and wound cleaning. The claimed solution may also contain a topical anesthetic, such as lidocaine hydrochloride, to provide relief from pain during treatment, and may be used as a carrier material for topical applications of medications including antibiotics and corticosteroids.

U.S. Pat. No. 5,536,742 discloses an anti-seborrhoeic composition containing both a broad spectrum antifungal drug and a topical antiseptic for the treatment of dogs. The composition can be formulated as a shampoo further containing a keratolytic or keratoplastic compound. The preferred antifungal drug is miconazole and the preferred topical antiseptic is chlorhexidine, and the formulation optionally contains selenium sulphide as an added ingredient.

U.S. Pat. No. 5,853,767, which is incorporated herein by reference, discloses a method for treating infections, bacterial, fungal and parasitic in origin, especially infections of organs such as the vagina and skin, is provided and involves administering to a patient in need thereof a composition comprising boric acid and acetic acid, in effective amounts. Such a composition is especially useful as a broad based treatment of vaginal infections of unknown bacterial or fungal origin and can be used without the need for medical diagnosis or while such a diagnosis is being determined. Such a composition is effective, safe, providing an alternative to existing forms of treatment which are toxic and is environmentally friendly.

US Publication No. 2008/0317737 discloses a topical treatment for skin disorders and diseases comprising a combination of at least one antifungal agent and at least one hydroxy acid agent formulated into shampoos, creams, lotions, gels, sprays, foams, pads, films, patches, and solutions for treatment of skin disorders and diseases in both humans and animals.

However, there remains a need for a composition with enhanced efficacy against the treatment of infections, whether bacterial, fungal, or parasitic, which preferably also has anti-inflammatory properties.

SUMMARY OF INVENTION

It is an object of the invention to provide a composition for the treatment of infections, especially skin and ear infections, including bacterial, fungal and parasitic infections, in humans and animals such as dogs, cats and horses.

It is another object of the invention to provide a topical composition comprising acetic acid, an antibacterial and/or an anti-fungal, and preferably also an anti-inflammatory.

It is another object of the invention to provide a composition for the treatment and prevention of bacterial, fungal and parasitic infections of the skin and ears with a composition comprising an antimicrobial, an antibacterial and/or an anti-fungal, an anti-inflammatory and/or antipruritic to provide itch relief often associated with skin and ear infections. According to a preferred embodiment, the antibacterial comprises boric acid. According to another preferred embodiment, the antifungal comprises at least one azole. According to yet another preferred embodiment, the anti-inflammatory comprises a corticosteroid.

It is another object of the invention to provide a composition comprising acetic acid, preferably in quantities of about 0.1% to about 10%, boric acid, preferably in quantities of about 0.1% to about 10%, and at least one azole, preferably present in quantities of about 0.01% to about 20%.

It is another object of the invention to provide a composition comprising acetic acid, preferably in quantities of about 0.1% to about 10%, boric acid, preferably in quantities of about 0.1% to about 10%, at least one azole, preferably in quantities of about 0.01% to about 20%, and a corticosteroid, preferably in quantities of about 0.01 to about 20%.

It is another object of the invention to provide a composition comprising acetic acid, preferably in quantities of about 0.1% to about 10%, boric acid, preferably in quantities of about 0.1% to about 10%, and a corticosteroid, wherein the corticosteroid is preferably present in quantities of about 0.01 to about 20%.

It is another object of the invention to provide a composition comprising acetic acid, preferably in quantities of about 0.1% to about 10%, and at least one azole, preferably in quantities of about 0.01% to about 20%.

It is another object of the invention to provide a composition comprising acetic acid, preferably in quantities of about 0.1% to about 10%, at least one azole, preferably in quantities of about 0.01% to about 20%, and a corticosteroid, preferably in quantities of about 0.01 to about 20%.

It is another object of the invention to provide a composition comprising acetic acid, preferably in quantities of about 0.1% to about 10%, at least one azole, preferably in quantities of about 0.01% to about 20%, and a topical antiseptic, preferably in quantities of about 0.1% to about 5%. According to a preferred embodiment, the topical antiseptic comprises chlorhexidine.

It is a further object of the invention to provide a composition for the treatment and prevention of infections formulated as a shampoo, a conditioner, a gel, a foam, a mousse, a spray, a dressing, a cream, a lotion, a serum, an otic, or a solution for topical or otic use as well as a material comprising the composition such as a wipe, a bandage, gauze, clothing, a drape, bedding, a dressing, a film, a pad or a patch.

It is a further object of the invention to provide a composition for the topical treatment and prevention of skin infections, including bacterial infections, such as pyoderma, and fungal infections, such as yeast (*Candida, Malassezia*), ringworm, dermatophytes, in humans and animals such as dogs, cats and horses.

It is a further object of the invention to provide a composition for the treatment and prevention of bacterial, fungal and parasitic infections of the skin further comprising a topical anesthetic to provide pain relief during treatment.

It is a further object of the invention to provide a composition for the treatment and prevention of both bacterial and fungal infections of the skin, including treatment of the feet, toes, skin folds, armpits, groin, buttock crease, breast folds, etc.

There has thus been outlined, rather broadly, the more important features of the invention in order that the detailed description thereof that follows may be better understood, and in order that the present contribution to the art may be better appreciated. There are, of course, additional features of the invention that will be described further hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may be readily utilized as a basis for the designing of other structures, methods and systems for carrying out the several purposes of the present invention. It is important, therefore, that equivalent constructions insofar as they do not depart from the spirit and scope of the present invention, are included in the present invention.

For a better understanding of the invention, its operating advantages and the aims attained by its uses, references should be had to the accompanying drawings and descriptive matter which illustrate preferred embodiments of the invention.

DETAILED DESCRIPTION OF PREFERRED EMBODIMENTS

The present invention relates to a composition for treatment of skin and ear infections, whether bacterial, e.g., including but not limited to pyoderma, or fungal, e.g., including but not limited to yeast, ringworm, dermatophytes, in humans and animals such as dogs, cats and horses, preferably with anti-inflammatory properties.

More specifically, the present invention relates to a composition with enhanced efficacy against fungi and yeasts comprising acetic acid, boric acid and at least one azole. According to the present invention, the acidification amplifies the effect of the azole(s).

According to a preferred embodiment, the composition comprises about 0.1% to about 10% acetic acid, about 0.1% to about 10% boric acid, and at least one azole, wherein the azole is preferably selected from the group consisting of abafungin, bifonazole, butoconazole, clotrimazole, econazole, fenticonazole, fluconazole, isoconazole, itraconazole, ketoconazole, miconazole, omoconazole, oxiconazole, posaconazole, ravuconazole, savuconazole, sertaconazole, sulconazole, terconazole, tioconazol, voriconazole, and mixtures thereof. However, according to the present invention, the azole may be selected from any class of azoles including pyrrole, pyrazole, imidazole, triazole, tetrazole, pentazole, oxazole, isoxazole, thiazole, isothiazole and mixtures thereof.

According to another preferred embodiment, the composition of the present invention may also contain about 0.01% to about 20% corticosteroid, such as hydrocortisone. According to this embodiment, the composition not only has antimicrobial effects, but also reduces inflammation, which is desirable as inflammation sometimes predisposes the skin to microbial infections. Although corticosteroids sometimes predispose the skin to infection, this effect is overcome in the present invention by the acetic acid and boric acid, which protect against yeast and bacteria, and the azole, which protects against fungi and yeast.

According to the present invention, the corticosteroid is preferably a topical steroid that may be selected from the group consisting of aclometasone dipropionate, amcinonide, betamethasone, betamethasone diproprionate, betamethasone sodium phosphate, betamethasone valerate, budesonide, clobetasol-17-propionate, clobetasone-17-butyrate, cortisone acetate, desonide, desoximetasone, dexamethasone, dexamethasone sodium phosphate, diflorasone diacetate, fluocinolone acetonide, fluocinonide, fluocortolone, fluocortolone caproate, fluocortolone pivalate, flurandrenolide, fluprednidene acetate, fluticasone propionate, halbetasol proprionate, halcinonide, hydrocortisone, hydrocortisone aceponate, hydrocortisone acetate, hydrocortisone buteprate, hydrocortisone-17-butyrate, hydrocortisone-17-valerate, methylprednisolone, methylprednisolone aceponate, mometasone, mometasone furoate, prednicarbate, prednisolone, prednisone, tixocortol pivalate, triamcinolone acetonide, triamcinolone, triamcinolone alcohol, and mixtures thereof.

Accordingly, according to a preferred embodiment, the composition of the present invention relates to a composition that combines the antipruritic and anti-inflammatory effects of a corticosteroid such as hydrocortisone with the antifungal/anti-yeast effects of anazole antifungal such as ketoconazole or miconazole, and the antimicrobial effects of acetic and boric acids. According to a further preferred embodiment, the present invention comprises about 1% acetic acid, about 2% boric acid, about 0.15% ketoconazole, and about 1% hydrocortisone.

According to a preferred embodiment, the composition is provided as a topical composition such as a shampoo or a spray for the topical treatment of bacterial and fungal infections, which also provides itch relief often associated with such conditions. The spray is preferably formulated as a leave-in, dry-on composition that is useful for focal infections, such as hot spots and inter-digital infections, where more frequent application is desired. The acetic acid has a conditioning and de-greasing (lipophilic) effect, making the coat or hair silky and luxurious while enhancing the effects of the azole such as ketoconazole.

According to another preferred embodiment, the composition is provided as an otic for the treatment, management and prevention of otitis. The otic solution of the present invention is useful for the initial management of disease as well as the prevention of recurrence of otitis. More specifically, the otic solution of the present invention may be used to assist in the initial management of otitis externa with yeast/ gram-positive bacteria and inflammation. For the treatment of such conditions, it is recommended that the ear(s) be treated 1-2 times a day for 7-10 days with the otic solution of the present invention. Further, use of the otic solution of the present invention should not stop once the infection is resolved, but should continue to help keep the ear comfortable and prevent recurrence. Moreover, in humans or animals with allergies, regular use (1-2 weekly) not only treats and helps prevent recurrent ear infections but helps reduce pruritus associated with allergies. In the case of an animal with a history of otitis externa, cleaning of the ears 1-2 a week on a long term basis is recommended to maintain comfort.

According to yet another preferred embodiment, the composition may be incorporated into a material such as a wipe, a bandage, gauze, clothing, a drape, bedding, a dressing, a film, a pad or a patch.

Example 1

Conditioner A

| Component | Quantity (% w/w) |
|---|---|
| Acetic acid | 1 |
| Boric acid | 2 |
| Ketoconazole | 0.15 |
| Hydrocortisone | 1 |

Example 2

Conditioner B

| Component | Quantity (% w/w) |
|---|---|
| Acetic acid | 1 |
| Boric acid | 2 |
| Ketoconazole | 0.2 |

Example 3

Shampoo A

| Component | Quantity (% w/w) |
|---|---|
| Acetic acid | 1 |
| Ketoconazole | 0.15 |
| Hydrocortisone | 1 |

Example 4

Shampoo B

| Component | Quantity (% w/w) |
|---|---|
| Acetic acid | 1 |
| Boric acid | 2 |
| Ketoconazole | 0.15 |
| Hydrocortisone | 1 |

Example 5

Wipes A

| Component | Quantity (% w/w) |
|---|---|
| Acetic acid | 1 |
| Ketoconazole | 1 |
| Hydrocortisone | 1 |

Example 6

Wipes B

| Component | Quantity (% w/w) |
|---|---|
| Acetic acid | 1 |
| Miconazole | 2 |
| Chlorhexidine | 2 |

Example 7

Otic A

| Component | Quantity (% w/w) |
|---|---|
| Acetic acid | 1 |
| Boric acid | 2 |
| Ketoconazole | 0.2 |
| Hydrocortisone | 1 |

Example 8

Otic B

| Component | Quantity (% w/w) |
|---|---|
| Acetic acid | 1 |
| Miconazole | 0.2 |

Of course, these compositions may also contain other components as appropriate that would be well known to one of ordinary skill in the art, such as solvents, excipients, surfactants, humectants, lubricants, thickeners, binders, foaming agents, preservatives, fragrances, etc. as well as analgesics, especially topical analgesics such as for example, benzocaine, butamben, dibucaine, lidocaine, oxybuprocaine, pramoxine, proparacaine, proxymetacaine or tetracaine, to provide pain relief during treatment.

Having now described a few embodiments of the invention, it should be apparent to those skilled in the art that the foregoing is merely illustrative and not limiting, having been presented by way of example only. Numerous modifications and other embodiments are within the scope of the invention and any equivalent thereto. It can be appreciated that variations to the present invention would be readily apparent to those skilled in the art, and the present invention is intended to include those alternatives.

Further, since numerous modifications will readily occur to those skilled in the art, it is not desired to limit the invention to the exact construction and operation illustrated and described, and accordingly, all suitable modifications and equivalents may be resorted to as falling within the scope of the invention.

What is claimed is:

1. A composition comprising about 1% acetic acid, about 2% boric acid, about 0.15% ketoconazole and about 1% hydrocortisone.

2. The composition of claim 1, wherein the composition comprises a shampoo, a conditioner, a mousse, a spray, an otic solution, a foam, a wipe, gauze, clothing, drapes, bedding, bandages, or dressings.

3. A method of treating a skin infection comprising topically applying the composition of claim 1.

* * * * *